(12) United States Patent
Yoder et al.

(10) Patent No.: US 7,244,427 B2
(45) Date of Patent: Jul. 17, 2007

(54) ISOLATED BOVINE IGG HEAVY CHAIN PROTEIN AND ITS USE AS AN ANTIMICROBIAL

(75) Inventors: Ralph D. Yoder, Ames, IA (US); Ronald E. Strohbehn, Ames, IA (US)

(73) Assignee: The Lauridsen Group Incorporated, Ankeny, IA (US)

( * ) Notice: Subject to any disclaimer, the term of this patent is extended or adjusted under 35 U.S.C. 154(b) by 1128 days.

(21) Appl. No.: 09/772,603

(22) Filed: Jan. 30, 2001

(65) Prior Publication Data

US 2002/0143157 A1   Oct. 3, 2002

(51) Int. Cl.
*A61K 39/395*   (2006.01)
*A61K 38/01*    (2006.01)
*C07K 16/00*    (2006.01)
*C07K 16/06*    (2006.01)

(52) U.S. Cl. ............................. 424/130.1; 530/387.1; 530/389.4

(58) Field of Classification Search ................ 436/547; 242/278.1
See application file for complete search history.

(56) References Cited

U.S. PATENT DOCUMENTS 5,871,731 A * 2/1999 Sprotte et al.
6,096,310 A * 8/2000 Bier et al.

OTHER PUBLICATIONS

Kempf et al., Transfusion 31(5): 423-27; 1991.*

* cited by examiner

*Primary Examiner*—Christina Chan
*Assistant Examiner*—Phuong Huynh
(74) *Attorney, Agent, or Firm*—Schwegman, Lundberg, Woessner & Kluth P.A.

(57) ABSTRACT

A new protein derived from acid hydrolyzed IgG concentrate which has a molecular weight of about 55,000, and is activated by heat within the defined narrow temperature range provides resulting product that has a protective mechanism for bacterial and viral invasion of living cells.

3 Claims, 1 Drawing Sheet

ISOLATED BOVINE IGG HEAVY CHAIN PROTEIN AND ITS USE AS AN ANTIMICROBIAL

FIELD OF THE INVENTION

This invention relates to a new protein derived from hydrolyzed bovine IgG concentrate that has independent characteristics significantly different from the protein that it was derived from, and which, by itself, can be used as an effective antimicrobial.

BACKGROUND OF THE INVENTION

There is a continuing effort and need for improved antimicrobials and antivirals which can be used with mammals, including humans, and domestic livestock, in order to modulate their immune system to improve their overall health and, for livestock, weight gain and efficiency. There have been some efforts in the past to use antibodies as immune system modulators.

Antibodies can be orally, intravenously or otherwise administered to a subject animal. This process is generally referred to in the art as passive transfer. The antibodies to be transferred generally are derived from milk, colostrum, serum, egg yolk and even monoclonal antibodies from hybridomas. An example of passive transfer occurs when maternal antibodies are passively transferred to newborn mammals through the placenta and during nursing through colostrum and milk. By this method, the young animals obtain protection and natural immunity against harmful antigens in the environment. Similarly, for developing avians, reptiles and other egg laying animals, egg yolk is the source of maternal antibodies.

Recently, therapeutic studies have successfully exploited oral administration of antibodies for the treatment of some infectious diseases. By a process of vaccination, animals can be immunized against specific microorganisms and other antigens. In addition, increased titers of antibodies can be obtained by a process of hyperimmunization. High amounts of specific antibodies can be obtained by immunizing animals with specific antigens and isolating the antibodies from the egg yolk, milk, colostrum or blood serum/plasma.

There are five distinct classes of antibodies which are also called immunoglobulins (Ig). The most abundant is IgG. The other four are IgM, IgA, IgD, and IgE. These antibodies combine with the antigen and act to neutralize or counter the effects of the antigen introduced into the animal. They accomplish this result by binding to the antigen, thereby neutralizing it and preventing it from binding to other specific cell receptors. The main immunoglobulin present in egg yolk is called IgY, which is similar to IgG, but possess considerable temperature and acid resistance.

Egg and milk preparations serve as a practical source of antibodies suitable for consumption by animals. In fact, egg yolks, for example, can contain as much as 100 mg of antibody, and large numbers of antibody-laden eggs can be produced in a relatively short period of time. Since vaccination of an animal can be used to develop such increased antibody titers in milk and eggs, such immunized milk and eggs can be fed to subject animals whereby antibodies are passively transferred to the subject animals to confer immunity and protection against microorganisms. Antibodies can be used not only to fight off pathogenic antigens or other foreign molecules, but can be used, as described herein, to neutralize naturally-occurring proteins, and thereby modulate that protein's normal physiological effect on the animal's system.

While in the past, bovine and porcine blood serum has been orally administered to aid domesticated livestock and the like in weight gain and overall health, to date, no one has isolated from the serum those fractions which provide specific desired benefits.

It goes without saying that an unexpected and unique advantage of isolation of protein fractions causing specific benefits would be the ability to dose precisely, and the ability to regulate specific responses of living cells to microbial agents such as bacteria and virus.

It is a primary objective of this invention to achieve specific protein fraction isolation and dosing with it to provide bacterial and viral resistance.

SUMMARY OF THE INVENTION

A unique, new protein isolate from the IgG fraction, which is an acid hydrolyzed IgG fraction that has been heat treated for from 15 minutes to 1 hour at a temperature of from 35° C. to 40° C. to unfold and modify the protein, making it antimicrobial in a manner not achievable by the original, untreated and unisolated IgG concentrate.

DETAILED DESCRIPTION OF THE PREFERRED EMBODIMENT

Figure 1:
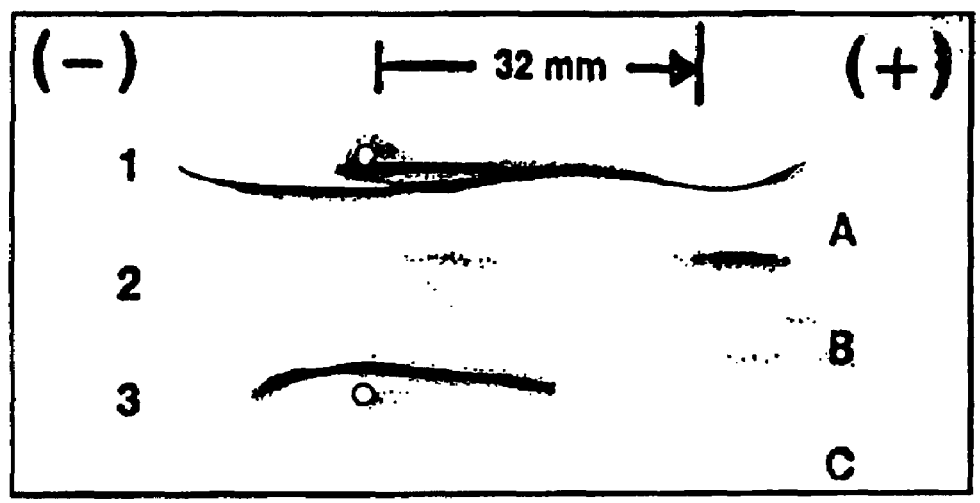
FIG. 1 shows the effect of acid treatment on the normal antigen-antibody activity of bovine IgG.

A new protein has been discovered as a result of a plan to acid hydrolyze bovine IgG concentrate, using, for example, hydrochloric acid. This protein has independent characteristics that are significantly different from the protein that it was derived from. In addition to its significant physical characteristics, the bioactivity of the protein, when used against seven enteric bacterial strains, shows that the new protein is bacterial static when incorporated into bacterial media that are appropriate for the test organisms. The growth of the test organisms, for example, has been reduced from 47.5% to 99.9% compared with controls. In tissue cultures that had been impregnated with the test protein and infected with four selected virus strains, the test protein reduced virus growth from 95% to 100% compared with the controls.

The invention provides for the first time a method where an essentially pure protein was separated from Bovine IgG concentrate which, when the protein was evaluated using the SDS-page electrophoresis, was shown to produce an intact protein that had a significantly different molecular weight than the starting material, but yet appears to be an intact, nearly pure protein.

The derived protein tested negative to a standard antigen-antibody reaction that is consistent with Bovine IgG concentrate. The protein was destroyed when heat denatured. This protein, when tested with 3 strains of pathogenic *E. Coli*, 2 strains of *Salmonella*, one of *pasteurella* and *Streptococcus* was bacterial static. When the same material was tested against 4 virus strains, it was viral static. This data will be provided below in the examples.

Also, as demonstrated in the examples, the bovine IgG concentrate, when sterile filtered and tested to determine if the intact bovine IgG protein was bacteria static like the acid treated soluble fraction, showed the whole protein concentrate was not bacteria static.

Briefly, the starting material is a commercially-available IgG fraction sold by American Protein Corporation, Ames, Iowa, under the trademark NUTRAGAMMIX™.

The starting material from which the IgG fraction is concentrated may be derived from bovine or porcine blood, colostrum or egg or whey. Preferably, it is bovine blood serum.

The initial concentrate is acid hydrolyzed slightly at elevated temperature in the first step of preparation of the new treated and isolated protein. Acid hydrolysis occurs for from about 15 minutes to about 1 hour at a temperature of from 35° C. to 40° C. Acid hydrolysis can occur with any inorganic acid, but is preferably hydrochloric, phosphoric or sulfuric acid at a range of from about 0.1 normal to about 0.2 normal. When this occurs, the concentrate turns quite viscous initially, and thereafter, upon neutralization back to a pH of about 7, becomes substantially less viscous. Thereafter, the material is centrifuged, and the supernatant contains the desired fraction of the present invention. This desired fraction is known to have a molecular weight of about 55,000, and can be used in liquid form, spray dried, or used with a suitable carrier, depending upon how and to whom it is dosed.

In use with domesticated livestock animals, it has been found that an amount should be dosed sufficient to provide a dosage of about 0.25 mg/ml of volume in the mammal's gut. Multiple dosing can occur with up to 5 grams/day. While the testing below-given is with respect to domesticated livestock, it can be used effectively as well on humans, as earlier indicated.

EXAMPLES

The following examples indicate bioactivity for humans as well as other mammalian species. They are offered to further illustrate but not limit the invention. Applicants intend to have the full range of equivalency allowed under the law with respect to the specification disclosure.

Sprayed dried bovine IgG concentrate was dissolved in 0.1 N HCL at 35° C. for 15 minutes. The solution was centrifuged at 10 K to remove the insoluble material. The solution was filtered through a filter series to 0.2 um. The resulting solution was tested for sterility by incubation in BHI for 48 hours at 37 C. Stock cultures of the test organisms were grown to $10^{10}$ per ml and used as the test bacteria. Three dilutions of the test protein were tested along with controls with each dilution inoculated with $10^3$ organisms/ml. The samples were inoculated at 37 C. for 14 to 18 hours, and the growth was counted using standard plate count methods.

Tissue culture cell lines were developed; VERO cells for human poliovirus as a model for enteric virus production, MDBK cells for herpes virus type 1 as a model for respiratory virus production, MA-104 cells for porcine (OSU strain) and human (WA strain) rotavirus as a model of viruses in neonates and young humans and animals. The test protein was included in the media for the tissue cultures, and the test virus was inoculated on the tissue culture including the controls. The plates were read when there was evidence of virus growth. The cultures were frozen and thawed three times, and the cell debris was removed with slow speed centrifugation. The amount of virus was then determined and compared with the controls.

The results from the acid treatment showed no antigen-antibody activity with the soluble protein after HCL treatment, FIG. 1.

Figure 2:
FIG. 2 shows the effect of the acid treatment of the invention on the molecular weight of the acid soluble fraction of bovine IgG protein.

The effect on the molecular weight of the acid soluble fraction of the bovine IgG protein can be seen in FIG. 2. In FIG. 2, band 1 shows the molecular weight of the concentrate itself. Band 2 shows the bovine globulin unreduced before acid treatment. Band 3 shows reduced bovine globulin. Band 4 shows bovine globulin plus hydrochloric acid unreduced, and band 5 shows reduced bovine globulin and acid hydrolyzation. A strong band in columns 4 and 5 at 55,000 can be seen.

The amino acid profile of the test protein before and after acid treatment is reported in Table 1. The results indicate that the test protein unexpectedly changed in amino acid profile after acid treatment. This demonstrates that the test protein not only lost confirmational structure as noted in FIGS. 1 and 2, but also amino acid profile which would change functionality.

The bacterial static impact of the test protein prepared as described above and as illustrated in FIG. 2 is shown in the following test results.

The hydrochloric acid treated and isolated IgG fraction was heated for 15 minutes at temperatures varying within the range of 35° C. to 40° C., thereafter neutralized, centrifuged, and the supernatant drawn off. This supernatant is approximately 35% of the pure bovine IgG concentrate.

It was tested in standard challenge tests with regard to its ability to reduce the bacterial growth, as illustrated in Table 1.

In particular, the test system occurred as follows:

The selected bacteria (see Table 2) were grown in TSB overnight to about $1 \times 10^9$/mL. The test medium was prepared with working stock concentrations of the test protein. The tubes were seeded with 1000 bacteria per mL and incubated at 37° C. for 20-24 h. The cultures were sampled and standard plate counts were performed.

TABLE 1

| AMINO ACID | MW | AMOUNT (In Mm) | AMOUNT (In mg/L) | MG AMINO ACID/g OF SAMPLE | % AMINO ACID |
|---|---|---|---|---|---|
| (ACIDIFIED) | | | | | |
| HYP | 131.1 | 0 | 0 | 0 | 0.00 |
| ASP | 133.1 | 0.015 | 1.9965 | 0.249138964 | 0.02 |
| SER | 105.1 | 0.013 | 1.3663 | 0.170497654 | 0.02 |
| GLU | 147.1 | 0.017 | 2.5007 | 0.312057003 | 0.03 |
| GLY | 75.07 | 0.01 | 0.7507 | 0.093678247 | 0.01 |
| HIS | 155.2 | 0 | 0 | 0 | 0.00 |
| TAU | 125.1 | 0 | 0 | 0 | 0.00 |
| ARG | 174.2 | 0.006 | 1.0452 | 0.130428272 | 0.01 |
| THR | 119.1 | 0.01 | 1.191 | 0.148622342 | 0.01 |
| ALA | 89.09 | 0.019 | 1.69271 | 0.21122966 | 0.02 |
| PRO | 115.1 | 0.01 | 1.151 | 0.143630828 | 0.01 |
| CYS | 240.3 | 0 | 0 | 0 | 0.00 |
| TYR | 181.2 | 0.005 | 0.906 | 0.113057802 | 0.01 |
| VAL | 117.1 | 0.01 | 1.171 | 0.146126585 | 0.01 |
| MET | 149.2 | 0 | 0 | 0 | 0.00 |
| LYS | 182.6 | 0.012 | 2.1912 | 0.27343516 | 0.03 |
| ILE | 131.2 | 0.005 | 0.656 | 0.081860837 | 0.01 |
| LEU | 131.2 | 0.013 | 1.7056 | 0.212838175 | 0.02 |
| PHE | 165.2 | 0.006 | 0.9912 | 0.123689727 | 0.01 |
| TOTAL | | | 19.31511 | 2.410291255 | 0.24 |

TABLE 1-continued

| AMINO ACID | MW | AMOUNT (In Mm) | AMOUNT (In mg/L) | MG AMINO ACID/g OF SAMPLE | % AMINO ACID |
|---|---|---|---|---|---|
| (NON-ACIDIFIED) | | | | | |
| HYP | 131.1 | 0 | 0 | 0 | 0.00 |
| ASP | 133.1 | 0.048 | 6.3888 | 7.627507163 | 0.76 |
| SER | 105.1 | 0.059 | 6.2009 | 7.40317574 | 0.74 |
| GLU | 147.1 | 0.058 | 8.5318 | 10.18600764 | 1.02 |
| GLY | 75.07 | 0.036 | 2.70252 | 3.226504298 | 0.32 |
| HIS | 155.2 | 0.012 | 1.8624 | 2.223495702 | 0.22 |
| TAU | 125.1 | 0 | 0 | 0 | 0.00 |
| ARG | 174.2 | 0.022 | 3.8324 | 4.575453677 | 0.46 |
| THR | 119.1 | 0.046 | 5.4786 | 6.540830946 | 0.65 |
| ALA | 89.09 | 0.042 | 3.74178 | 4.46726361 | 0.45 |
| PRO | 115.1 | 0.033 | 3.7983 | 4.53474212 | 0.45 |
| CYS | 240.3 | 0 | 0 | 0 | 0.00 |
| TYR | 181.2 | 0.018 | 3.2616 | 3.893982808 | 0.39 |
| VAL | 117.1 | 0.045 | 5.2695 | 6.291189112 | 0.63 |
| MET | 149.2 | 0.005 | 0.746 | 0.890639924 | 0.09 |
| LYS | 182.6 | 0.036 | 6.5736 | 7.848137536 | 0.78 |
| ILE | 131.2 | 0.014 | 1.8368 | 2.192932187 | 0.22 |
| LEU | 131.2 | 0.043 | 5.6416 | 6.735434575 | 0.67 |
| PHE | 165.2 | 0.019 | 3.1388 | 3.747373448 | 0.37 |
| TOTAL | | | 69.0054 | 82.38467049 | 8.24 |

TABLE 2

THE % REDUCTION OF BACTERIAL GROWTH AFTER TREATMENT WITH THE TEST PROTEIN

| TEST BACTERIA | CONTROL MEDIA NUTRIENTS TO GROW | SUPERNATANT 0.25 MG/ML OF TEST PROTEIN | SUPERNATANT 0.12 MG/ML OF TEST PROTEIN | SUPERNATANT 0.06 MG/ML OF TEST PROTEIN |
|---|---|---|---|---|
| E. COLI 055 | 0% | 97% | 34% | 0% |
| E. COLI 0111 | 0% | 91% | 15% | 15% |
| E. COLI 0157:H7 | 0% | 89% | 29% | 22% |
| SALMONELLA TYPHIMURIUM | 0% | 96.5% | 87.5% | 54.5% |
| SALMONELLA JAVIANAI | 0% | 75.4% | 57.5% | 47% |
| PASTEURELLA SP. | 0% | 47.5% | 47.5% | 0% |
| STREPTOCOCCUS SUIS | 0% | 99.9% | 99.9% | 99.5% |

It can be seen that the test protein significantly reduced the growth of all the test organisms with the least effect shown against pasteurella species.

Similar challenges using the following protocol were tested against viruses in vitro. In particular, the ability of acid digested test protein preparations to inhibit the production of virus in vitro were tested. Four virus-cell systems were tested under this program: Human poliovirus on vero cells as a model of enteric virus production; bovine herpesvirus type 1-MDBK cells as a model of respiratory virus production; and porcine (OSU strain) and human (WA strain) rotavirus on MA-104 cells as a model of viruses which are common problems in neonates and young humans and animals. The basic design of the experiments was simple: A small inoculum (~1000 TCID) of each virus on cells in unsupplemented medium was used as control, and the same inoculum on cells in medium supplemented with 3%, 1.5% or 0.75% of each acid digested (dissolved) test protein preparation. The cultures were run until significant indication of viral infection was observed in the unsupplemented cultures. The cultures were then frozen and thawed three times, the cell debris removed by low speed centrifugation, and the amount of virus assessed. All experiments were run in duplicate. This system was chosen to minimize the effects of the test protein preparations on measurement of the virus. This method gives a fairer comparison of the amount of virus produced than earlier methods we have used. Under other systems we have experienced inhibition of the detection of virus by the preparations under test.

Table 3 shows the results of this testing.

TABLE 3

THE PERCENT REDUCTION OF IN VITRO VIRAL GROWTH AFTER TREATMENT WITH THE TEST PROTEIN

| VIRUS | CONTROL | TEST PROTEIN @ 3% OF MEDIA |
|---|---|---|
| POLIO VIRUS | 0% | 92% |
| BOVINE HERPES VIRUS | 0% | 90% |
| PORCINE ROTOVIRUS (OSU) STRAIN | 0% | 100% |
| HUMAN ROTOVIRUS | 0% | 100% |

The test protein significantly stopped the infection rate of virus particles compared to the controls. Importantly, when the intact bovine IgG concentrate was evaluated for viral static capacity, it was negative.

In a chicken feeding test the IgG concentrate, as described above, was compared with a controlled plasma and a negative control. Chicks fed the acid-treated plasma at 4% of the ration gained significantly (P<0.05) faster compared with the controls.

In follow-up tests, the IgG concentrate was tested against a pair of E-Coli bacteria. An antibiotic, gentamicin, sensitive parent and mutation that was resistant to the antibiotic were used to test the growth-inhibiting effects of the new protein. The summary of the results are shown in the following Table 4.

TABLE 4

% REDUCTION OF BACTERIAL GROWTH AFTER TREATMENT WITH THE TEST PROTEIN

| SENSITIVE STRAIN | SENSITIVE STRAIN PLUS TEST PROTEIN | RESISTANT STRAIN PLUS TEST PROTEIN | RESISTANT STRAIN PLUS ANTIBIOTIC |
|---|---|---|---|
| 0 | 97% | 97% | 0 |

The results on Table 4 show that the IgG concentrate treated and isolated as herein described controls the rate of growth of both the resistant and the sensitive strain of *E-Coli*, and that the resistant strain's growth was not restricted in the presence of the antibiotic.

This is a significant development because of the antibiotic resistance that has been developing since antibiotics have been used over a long period of time. This finding strongly suggests that the mode of action of this concentrate is significantly different from that of antibiotics in general, and specifically gentamicin.

From the above it can be seen that the invention accomplishes at least all of its stated objectives.

What is claimed is:

1. A method of providing bacterial static and viral static activity, comprising:

oral dosing of a mammal with an anti-bacterial and antiviral effective amount of a treated, isolated and neutralized IgG fraction that has a molecular weight of about 55,000, which has been treated by acid hydrolysis, heated from 15 minutes to 1.0 hour at a temperature of 35° C. to 40° C. and thereafter neutralized back to a pH of about 7.

2. The method of claim 1 wherein the amount dosed is sufficient to provide a dosage of 0.25 mg/ml in the mammal's gut.

3. The method of claim 1 wherein the dose is up to 5 grams/day.

* * * * *

UNITED STATES PATENT AND TRADEMARK OFFICE
CERTIFICATE OF CORRECTION

PATENT NO.       : 7,244,427 B2                                          Page 1 of 1
APPLICATION NO.  : 09/772603
DATED            : July 17, 2007
INVENTOR(S)      : Yoder et al.

It is certified that error appears in the above-identified patent and that said Letters Patent is hereby corrected as shown below:

On the Title page, item (54), in column 1, line 1, delete "IGG" and insert -- IgG --, therefor.

In column 1, line 1, delete "IGG" and insert -- IgG --, therefor.

In column 2, line 56, delete "SDS-page" and insert -- SDS-Page --, therefor.

In column 2, line 64, delete "pasteurella" and insert -- Pasteurella --, therefor.

In column 3, line 50, delete "37 C." and insert -- 37 °C. --, therefor.

In column 3, line 54, delete "37 C." and insert -- 37 °C. --, therefor.

In column 5, line 47, delete "pasteurella" and insert -- Pasteurella --, therefor.

Signed and Sealed this

Twentieth Day of November, 2007

JON W. DUDAS
*Director of the United States Patent and Trademark Office*